United States Patent [19]

Churchill et al.

[11] Patent Number: 4,526,938

[45] Date of Patent: Jul. 2, 1985

[54] CONTINUOUS RELEASE FORMULATIONS

[75] Inventors: Jeffrey R. Churchill, Northwich; Francis G. Hutchinson, Lymm, both of United Kingdom

[73] Assignee: Imperial Chemical Industries PLC, London, England

[21] Appl. No.: 485,454

[22] Filed: Apr. 15, 1983

[30] Foreign Application Priority Data

Apr. 22, 1982 [GB] United Kingdom ............... 8211704

[51] Int. Cl.$^3$ .................. C08L 5/02; C08L 51/00; C08L 71/02; C08L 79/00
[52] U.S. Cl. .................... 525/415; 525/54.1; 525/54.2; 525/154; 525/386; 525/403; 525/405; 525/450; 525/462; 525/472; 525/57; 527/200; 527/300
[58] Field of Search .............. 525/415, 54.1, 403, 525/410, 411, 412, 54.2, 57, 462, 450, 154, 405, 472, 386; 527/200, 300

[56] References Cited

U.S. PATENT DOCUMENTS

| | | | |
|---|---|---|---|
| 3,773,919 | 11/1973 | Boswell | 424/19 |
| 3,887,699 | 6/1975 | Yolles | 424/19 |
| 4,045,418 | 8/1977 | Sinclair | 525/415 |
| 4,157,437 | 6/1979 | Okazumi | 525/415 |
| 4,243,775 | 1/1981 | Rosensaft | 525/415 |
| 4,279,249 | 7/1981 | Vert | 525/415 |
| 4,429,080 | 1/1984 | Casey | 525/415 |

FOREIGN PATENT DOCUMENTS

| | | |
|---|---|---|
| 2849785 | 5/1979 | Fed. Rep. of Germany ...... 525/415 |
| 1325209 | 8/1973 | United Kingdom . |
| 1351409 | 5/1974 | United Kingdom . |
| 1388580 | 5/1975 | United Kingdom . |

OTHER PUBLICATIONS

Remingtons Pharmaceutical Sciences, Mack Publ. Co., (1975), pp. 1618–1631.
Jackanicz et al., Contraception, 1973, (8), 227–234.
Anderson et al., Contraception, 1976, (11), 375–384.
Wise et al., Life Sciences, 1976, (19), 867–874.
Woodland et al., J. of Medicinal Chemistry, 1973, 16, 897–901.
Wise et al., Bulletin of the Parenteral Drug Assn., 1976, (30), pp. 306–312.

*Primary Examiner*—Allan M. Lieberman
*Attorney, Agent, or Firm*—Cushman, Darby & Cushman

[57] ABSTRACT

Pharmaceutical compositions comprising a pharmacologically active polypeptide and a pharmacologically or veterinarily acceptable amphipathic, non-cross-linked linear, branched or graft block copolymer, which has a minimum weight average molecular weight of 5,000, in which the hydrophobic component is biodegradable and the hydrophilic component may or may not be biodegradable, the composition being capable of absorbing water to form a hydrogel when placed in an aqueous, physiological-type environment; copolymers suitable for use in said compositions; and method for the manufacture of such copolymers.

4 Claims, No Drawings

CONTINUOUS RELEASE FORMULATIONS

This invention relates to pharmaceutical compositions of pharmacologically-active polypeptides, which provide continuous release of the polypeptide over an extended period when the composition is placed in an aqueous, physiological-type environment.

It has long been appreciated that the continuous release of certain drugs over an extended period following a single administration could have significant practical advantages in clinical practice, and compositions have already been developed to provide extended release of a number of clinically useful drugs, after oral dosing (see, for example, Remington's Pharmaceutical Sciences, published by Mack Publishing Company, Easton, Pa., U.S.A., 15th Edition, 1975, pages 1618–1631), after parenteral administration (ibidem, pages 1631–1643), and after topical administration (see, for example, United Kingdom Pat. No. 1,351,409). A suitable method of parenteral administration is the subdermal injection or implantation of a solid body, for example a pellet or a film, containing the drug, and a variety of such implantable devices have been described. In particular, it is known that, for many drugs, suitable implantable devices for providing extended drug release may be obtained by encapsulating the drug in a biodegradable polymer, or by dispersing the drug in a matrix of such a polymer, so that the drug is released as the degradation of the polymer matrix proceeds.

Suitable biodegradable polymers for use in such substained release formulations are well known, and include polyesters which gradually become degraded by hydrolysis when placed in an aqueous, physiological-type environment. Particular polyesters which have been used are those derived from hydroxycarboxylic acids, and much prior art has been directed to polymers derived from α-hydroxycarboxylic acids, especially lactic acids in both its racemic and optically active forms, and glycolic acid, and copolymers thereof—see, for example, U.S. Pat. Nos. 3,773,919 and 3,887,699; Jackanicz et al., Contraception, 1973, 8, 227–234; Anderson et al., ibidem, 1976, 11, 375–384; Wise et al., Life Sciences, 1976, 19, 867–874; Woodland et al., Journal of Medicinal Chemistry, 1973, 16, 897–901; Yolles et al., Bulletin of the Parenteral Drug Association, 1976, 30, 306–312; Wise et al., Journal of Pharmacy and Pharmacology, 1978, 30, 686–689 and 1979, 31, 201–204.

United Kingdom Patent Specification No. 1,325,209 (equivalent to U.S. Pat. No. 3,773,919) and U.S. Pat. No. 3,887,669 make reference to extended or sustained release of polypeptides. The latter mentions insulin only, but it contains no specific example of any such formulation, and the reference to polypeptides is apparently entirely speculative, appearing, as it does, only in an extensive listing of very many different classes of drugs which can allegedly be incorporated into formulations of the kind described therein. In fact, essentially all of the other drug types referred to in that specification, apart from polypeptides, are relatively hydrophobic in character and of relatively low molecular weight, and the disclosure of that specification displays no recognition of the difficulties which we have encountered when seeking to obtain satisfactory sustained release formulations of polypeptides, many of which are relatively hydrophilic, and of relatively high molecular weight.

It is to be appreciated that "sustained" or "extended" release of a drug may be either continuous or discontinuous. We have now discovered, in fact, that in many cases when the teaching of the prior art, and in particular the teaching of United Kingdom Specification No. 1,325,209, is applied to the manufacture of a formulation of a polypeptide, the release of the polypeptide from the formulation, although occurring over an extended period of time, may also be discontinuous. For example, the release of a polypeptide from a polylactide polymer as described in the said Specification is often preceded by a significant induction period, during which no polypeptide is released, or is polyphasic, and comprises an initial period during which some polypeptide is released, a second period during which little or no polypeptide is released, and a third period during which most of the remainder of the polypeptide is released. By contrast, it is an object of the present invention to provide compositions of polypeptides from which, apart possibly from a relatively short initial induction period, the polypeptide is released continuously, with no periods during which little or no polypeptide is released. The words "continuous release" are used in this specification solely to describe a release profile which is essentially monophasic, although it may have a point of inflection, but certainly has no "plateau" phase.

United Kingdom Patent Specification No. 1,388,580 describes sustained release formulations containing insulin, which are based on hydrogels formed by reacting a water soluble polymer with a chelating agent, then cross linking the polymer-chelating agent chains by reaction with a polyvalent metal ion in aqueous solution to form a hydrogel. Insulin was incorporated in a preformed hydrogel in aqueous solution, and the whole was homogenised and injected sub-cutaneously or intramuscularly.

It is an object of the present invention to provide an implantable or injectable pharmaceutical or veterinary formulation for pharmacologically useful polypeptides, which is in solid form, and which absorbs water from the animal body, after implantation, to form a hydrogel from which the polypeptide is released continuously over an extended period of time.

Thus, according to the present invention, there is provided a pharmaceutical composition comprising a pharmacologically useful polypeptide and a pharmaceutically or veterinarily acceptable amphipathic, non-cross-linked linear, branched or graft block copolymer, which has a minimum weight average molecular weight of 5,000, in which the hydrophobic component is biodegradable or hydrolytically unstable under normal physiological conditions, and the hydrophilic component may or may not be biodegradable, the composition being capable of absorbing water to form a hydrogel when placed in water or an aqueous physiological type environment.

This invention is applicable to polypeptides quite generally, without any limitation as to structure or molecular weight, but is most useful for polypeptides which are relatively hydrophilic, and the following list, which is not intended to be exhaustive, is indicative of polypeptides which may be employed in the formulation of this invention:

oxytocin, vasopressin, adrenocorticotrophic hormone (ACTH), epidermal growth factor (EGF), prolactin, luliberin or luteinizing hormone releasing hormone (LH-RH), growth hormone, growth hormone releasing factor, insulin, somatostatin, glucagon, interferon, gastrin, tetragastrin, pentagastrin, urogastrone, secretin, calcitonin, enkephalins, endorphins, angiotensins, renin, bradykinin, bacitracins, polymyxins, colistins, tyrocidin, gramicidines, and synthetic analogues and modifications and pharmaceutically-active fragments thereof, monoclonal antibodies and soluble vaccines.

A particular LH-RH analogue to which this invention is applicable is ICI.118,630,

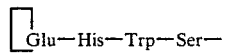

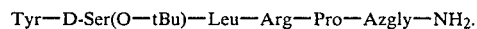

By "an aqueous phydiological type environment" we mean the body, particularly the musculature or the circulatory system, of a warm-blooded animal, although in laboratory investigations such an environment may be mimicked by aqueous liquids, optionally buffered to a physiological pH, at a temperature of between 35° and 40° C.

The continuous release composition of the invention may be placed in the body of an animal which it is desired to treat with a polypeptide by, for example, intramuscular or subcutaneous injection, or by sub-dermal surgical implantation, in conventional clinical or veterinary manner.

The pharmaceutically or veterinarily acceptable amphipathic copolymer may be, for example, a linear block copolymer of the formula $A_m(BA)_n$ or $B_m(AB)_n$ wherein m is 0 or 1, n is an integer, A is a pharmaceutically or veterinarily acceptable hydrophobic polymer and B is a pharmaceutically or veterinarily acceptable hydrophilic polymer, or the amphipathic copolymer may be a graft or branched block copolymer of the formula $AB_n$ or $BA_n$ wherein A, B and n have the meanings stated above, and wherein respectively either A or B is a backbone polymer with n units of a monomer or polymer B or A respectively grafted onto it.

The pharmaceutically or veterinarily acceptable hydrophobic polymer A may be, for example, poly-(D-, L- or DL-lactic acid), poly(D-, L- or DL-lactide), polyglycolic acid, polyglycolide, poly-ε-caprolactone, poly(3-hydroxybutyric acid) or a non-therapeutic hydrophobic polypeptide, for example polybenzylglutamate. Alternatively, the hydrophobic polymer A may be a polyacetal of the general formula:

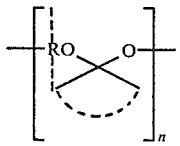

wherein R is a hydrocarbon radical, or a polycarbonate or polyorthoester of the general formula:

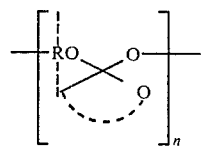

wherein R is a hydrocarbon radical, as described in U.S. Pat. No. 4,093,709, which is incorporated herein by reference, or it may be a copolymer comprising such acetal, carbonate, or ortho-ester units alternating with diol units, or it may be a copolymer of the formula:

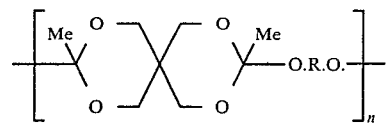

which is obtained by reacting pentaerythritol with ketene to form 3,9-bis(methylene)-2,4,8,10-tetraoxaspiro[5,5]undecane which is then copolymerised with a diol HO—R—OH, as described in Journal of Polymer Science, Polymer Letters, 1980, pages 619–624. The diol HO—R—OH may be, for example, a high molecular weight polyethylene glycol or a mixture of that with low molecular weight species, giving a random structure. The hydrophobic polymer may also itself be a copolymer derived from two or more monomers from which the above polymers are derived.

The pharmaceutically or veterinarily acceptable hydrophilic polymer B may be, for example, polyvinyl alcohol, polyvinylpyrrolidone, polyethylene oxide, polyethylene glycol, polyacrylamide, polymethacrylamide, dextran, alginic acid, sodium alginate, gelatine or a copolymer of two or more of the monomers from which the above polymers are derived.

In a further alternative, the hydrophilic polymer B may itself be a copolymer, for example a polyoxyethylene/polyoxypropylene block copolymer of the type known as "Pluronics" (trade mark) or "Synperonics" (trade mark).

Various mechanisms by which drugs are released from biocrodible polymers are described in "Controlled Release of Biactive Materials", edited by R. Baker, Academic Press 1980, particularly chapter 1, pages 1–17, by J. Heller and R. W. Baker.

In the present invention, when the dry amphipathic copolymer, containing a polypeptide, is immersed in water or placed in an aqueous physiological environment within an animal body, water uptake is a function of the hydrophilic or water-interactive parts of the copolymer, and the material swells. This absorption of water, however, renders the water-insoluble parts of the copolymer incompatible, and these hydrophobic parts of the copolymer then serve as cross-linking points, which thus serve to limit further water uptake. In this swollen, hydrated state, the matrix is permeable to water-soluble polypeptides incorporated within the matrix, and such polypeptides are thus progressively desorbed from the matrix.

In the process of swelling, and when swollen to some equilibrium state, hydrolytic degradation of the hydrophobic part of the copolymer starts to occur. The partially degraded copolymer has greater swellability, so that continued hydrolysis leads to progressively further water uptake, an increasingly water-permeable matrix, and a further increase in polypeptide desorption which compensates for its decreasing concentration and maintains its continuous release. Thus, by appropriate design of the copolymer material, the initial swelling to a hydrogel and consequent desorption of active material, and the rate of subsequent hydrolytic degradation to increase the further desorption of active material to compensation for its decreasing concentration in the matrix, can be controlled so as to give continuous release of active material over an extended period of time, as defined above.

Such an ideal release profile for the active material can also be obtained by blending different copolymers, each having its own defined properties (for example, molecular weight, molecular weight distribution, block structure, hydrophilicity, degradation properties, diffusional properties), and by appropriate combination of different such materials, the rate of release, and the duration of release, of an active material can be varied as desired.

Also by appropriate choice of the above parameters, and/or appropriate blending, a copolymer material can be obtained which allows of processing into implants at relatively low temperatures, certainly below 100° C., and in some cases even at room temperature, and is thus suitable for the fabrication of implants incorporating heat sensitive or solvent sensitive polypeptide active materials. For example, block copolymers of polyethylene glycol and amorphous hydrophobic polymers, having a glass transition temperature above 37° C., are particularly useful, because the polyethylene glycol block plasticises the hydrophobic block, giving a material which is readily processed at relatively low, even at room temperature, while on subsequent standing the polyethylene glycol blocks crystallise to give a tough hard product which can be easily handled.

The block copolymers defined above are themselves novel, useful materials, per se. Thus, according to a further feature of the invention, there is provided a pharmaceutically or veterinarily acceptable amphipathic linear, branched or graft block copolymer, which has a minimum weight average molecular weight of 5,000, in which the hydrophobic component is biodegradable or hydrolytically unstable under normal physiological conditions, and the hydrophilic component may or may not be biodegradable, and which copolymer is capable of absorbing water to form a hydrogel when placed in water on an aqueous environment.

Particular such copolymers are those defined above.

According to a further feature of the invention, there is provided a blend of two or more such copolymers as defined above.

These copolymers and copolymer blends are also useful more generally for the continuous release of nonpeptide drugs by oral, including intra-ruminal, parenteral, ocular, rectal or vaginal administration.

Thus, according to further features of this invention there are provided pharmaceutical or veterinary compositions comprising a non-peptide pharmacologically-active compound and a block copolymer as defined above, and the use of such block copolymers for the continuous release of such a non-peptide, pharmacologically-active compound.

According to a further feature of the invention, there is provided a process for the manufacture of a pharmaceutically or veterinarily acceptable amphipathic linear, branched or graft block copolymer as defined above, which comprises copolymerising monomer A and monomer B by conventional techniques such as graft copolymerisation, polycondensation and polyaddition, optionally with an appropriate catalyst, for example zinc oxide, zinc carbonate, basic zinc carbonate, diethyl zinc, organotin compounds, for example stannous octoate (stannous 2-ethylhexanoate), tributylaluminium, titanium, magnesium or barium compounds or litharge, and of these stannous octoate is generally preferred.

The copolymerisations are otherwise carried out in conventional manner, known in the polymer art, as regards time and temperature.

The invention is illustrated but not limited by the following Examples:

EXAMPLE 1

Polyethylene glycol of molecular weight 20,000 (30 g.) was stirred and heated under vacuum (<0.1 mm. of mercury) at 120° C. for 3 hours. D,L-lactide (15 g.) and glycolide (15 g.) were added, and the mixture was stirred under a nitrogen atmosphere until the solids melted. The temperature was raised to 160° C., and stannous octoate (stannous 2-ethylhexanoate) (0.1 ml.) was added. The mixture was maintained at 160° C. for 3 hours, by which time it had become highly viscous, and it was then cooled and dissolved in acetone (200 ml.). This acetone solution was added slowly to vigorously stirred ethanol (1500 ml.), and the precipitate thus produced was filtered off, and dried in a vacuum oven for 3 hours at room temperature, then overnight at 40° C.

The n.m.r. spectrum of this copolymer, in deuteriochloroform, showed it to have the composition oxyethylene:lactic:glycolic of 2:1:1.

This copolymer was moulded at about 60° C. to a soft, plastic transparent film. A sample (39 mg.) swelled rapidly when placed in water, taking up 135 mg. of water over 4 hours, to give a transparent hydrogel which subsequently disintegrated over 2 weeks at 37° C.

EXAMPLE 2

The polymer described in Example 1 (20.2 mg.) and bovine growth hormone (BGH), (5.1 mg.) were blended together at about 40° C. to give an opaque blend, which was moulded into a slab 1 mm. thick. This slab was immersed in a buffer solution at pH 8.6 (M/15 buffer, pH 8.6, containing 0.01% sodium azide), and released a material of molecular weight about 22,000 which had the same retention time on high pressure liquid chromatography as BGH, over a period of at least 12 days.

EXAMPLE 3

Using the process described in Example 2, the copolymer/BGH blend was formed into discs weighing about 45 mg. and containing about 20% of BGH. When such discs were implanted, each in a hypophysectomised rat, the animals' weights increased by an average of 25% over 7 days, whereas the weights of control animals each given a placebo implant remained virtually unchanged.

EXAMPLE 4

The copolymer described in Example 1 (13.5 mg.) and monoclonal mouse immunoglobulin A, (IgA), with a defined antigen specificity and a molecular weight of >180000 (1.5 mg.) were blended at 50° C. to give a homogeneous mixture of the IgA in the copolymer, and the protein/copolymer mixture was moulded to give a sphere of ~2 mm. diameter. The in vitro release of IgA was evaluated by immersing the protein copolymer in buffer (phosphate buffered saline, pH 7.2) at 37° C. Using an enzyme linked immunoassay technique the aqueous medium was assayed for active IgA, and release of the biologically active protein was shown to start after 2 days and continue for at least 9 days.

EXAMPLE 5

Polyethylene glycol having a molecular weight of 20000 (50 g.) was dissolved in chloroform (150 mg.) and washed six times with distilled water (~300 ml.), discarding the aqueous washes. The chloroform was evaporated under reduced pressure and the purified polyethylene glycol was dried at 160° C./0.05 mm.Hg. for 1 hr.

Stannous octoate (stannous 2-ethylhexanoate) (~5 g.) was purified by heating at 140° C./0.055 mm.Hg. to remove impurities. The purified polyethylene glycol (14.3 g.) was heated to 160° C. under vacuum (0.05 mm.Hg.) in a 100 ml. round bottomed flask for 1 hr. Freshly prepared, pure D,L-lactide (42.9 g.) was added under nitrogen and melted at 160° C. Stannous octoate (0.2 ml.) was added, and the mixture was stirred until the viscosity no longer allowed stirring to continue. After 3 hrs., a highly viscous product was obtained. The mixture was allowed to cool, the flask was broken, the contents of the flask were dissolved in acetone (~300 ml.) and the solution was filtered. The filtrate was added slowly to ethanol (~1000 ml.) with vigorous agitation to give a fibrous precipitate, which was collected and dried at 30° C. in a vacuum oven overnight. Analysis of the product by n.m.r. showed the product to have a composition of oxyethylene:lactic of 1:3, and the intrinsic viscosity in chloroform was 1.055.

The product was moulded to a thin (0.2 mm.), soft, plastic transparent film. On immersion in water, the film (0.54 g.) increased in weight to 0.95 g. in 1 day at 37° C. The hydrated transparent film had rigidity and strength superior to the initially dry copolymer. After 35 days, the film was intact and retained good mechanical properties showing that the copolymer was being degraded only slowly, as shown by change of composition by n.m.r.

When bovine growth hormone is incorporated into the dry copolymer at 60° C., the resulting polypeptide/-polymer blend releases a 22000 molecular weight product into buffer (M/15 phosphate buffer, pH 8.6) over at least 7 days.

EXAMPLE 6

Polyethylene glycol having a molecular weight of 6000 (50 g.) was purified using the method described above in Example 5.

The purified dry polyethylene glycol (7.5 g.) and stannous chloride dihydrate (15 mg.) were mixed at room temperature then heated with stirring to 155° C. under high vacuum (0.1–0.01 mm.Hg.) and maintained at this temperature for 2 hrs. while freshly prepared, dry D,L-lactide (22.5 g.) was added to the mixture under nitrogen, and melted. The reaction temperature was maintained at 155°–160° C. for 3 hrs. to give a viscous product, which was poured onto poly-tetrafluoroethylene film and allowed to cool. The polymeric product was dissolved in acetone (70 ml.) with warming, and the polymer was isolated by pouring the acetone solution into ethanol (600 ml.). The precipitate was dried in a vacuum oven overnight at 60° C. The polymer had an intrinsic viscosity in chloroform of 0.41. When pressed as a thin film (0.2 mm.) and immersed in water, the polymer takes up approximately its own weight of water at 37° C. over 24 hrs. to give a tough hydrogel.

EXAMPLE 7

99 Mg. of a block copolymer as prepared in Example 6 containing 25 parts of polyethylene glycol (mol. wt. 6000) and 75 parts of poly(D,L-lactide) was dissolved in 4.5 ml. of anhydride free glacial acetic acid and 0.5 ml. of distilled water. 200 µL. of a solution containing 1.1 mg. of mouse epidermal growth factor (EGF) was added to the polymer solution, and the mixture was homogenised. The homogenised solution was frozen and then freeze dried for 18 hrs., the product was moulded at 50° C. to give an implant weighing 40 mg. (~8 mm.×4 mm.×1 mm). The implant was placed in 1 ml. of human serum at 37° C., and the release of EGF was measured by radio immunoassay on aliquots of serum. The results showed a continuous release of peptide over at least three days.

EXAMPLE 8

25 G. of a copolymer containing equimolar proportions of D,L-lactide and glycolide and having an intrinsic viscosity in chloroform of 0.20 was dissolved in 50 ml. of dry ethyl ecetate, and the solution was heated to reflux with stirring under nitrogen. 0.25 G. of lauroyl peroxide was dissolved in freshly distilled vinyl pyrrolidone (25 ml.). The mixture was added dropwise to the refluxing polymer over 2 hrs., and the mixture ws heated at reflux for a further 6 hrs. On cooling, the mixture gelled. Purification of the amphipathic block graft copolymer by removal of homo polymer of polyvinyl pyrrolidone using precipitation techniques was difficult as precipitation often resulted in colloidal suspensions, and this indicated that grafting of polyvinyl pyrrolidone to the lactide/glycolide copolymer had occurred.

The ethyl acetate mixture was therefore warmed to 70° C. and 50 ml. of ethanol was added to give a colloidal suspension, from which the polymer was isolated by precipitation into n-hexane (2 liters). The polymer thus obtained was dried at 90° C. overnight under vacuum to give on cooling a brittle product consisting of graft copolymer and homo polyvinylpyrrolidone. The product had an intrinsic viscosity of 0.29 in chloroform, and approximately 50% of polyvinyl-pyrrolidone as homocopolymer and graft block copolymer.

The polymer thus obtained (0.45 g.) and ICI. 118,630 (0.05 g.) were dissolved in anhydride-free glacial acetic acid (5 ml.) and freeze dried at 0.01 mm. of mercury for 22 hr.

The product was moulded at 110° C. for 20 secs. to give a slab (~0.8 cm.×1.2 mm.×2 mm., weighing 30 mg.) which, when immersed in aqueous pH 7.4 buffer at 37° C. released the peptide over a period of several days.

EXAMPLE 9

50 G. of polyvinyl alcohol having a molecular weight of 14,000 was dissolved in 500 g. of commercial D,L-lactic acid (containing ~12% water) with stirring under nitrogen. The mixture was heated to 140° C. and water was distilled off over 8 hrs., during which time the mixture became progressively more viscous and its temperature rose to 190° C. When no further water distilled over, the pressure was reduced to ~25 cm. of mercury, and the mixture was heated for a further 8 hrs. Finally, the pressure was reduced to 0.1 mm. of mercury and the mixture was heated at 200° C. for 8 hrs. to give a highly viscous amber product.

The polymer was allowed to cool, and the flask was broken. The product was broken up into small pieces and dissolved in methanol (1.5 liters), and the product was isolated by precipitate in 10 liters of distilled water.

The precipitation was washed with a further 5 liters of water, and dried under vacuum at room temperature for 8 hrs., finally at 100° C. for 16 hrs., to give an amber glassy product which consisted of a polyvinyl alcohol back-bone containing pendant polylactic acid chains of low molecular weight, intrinsic viscosity=0.65 in chloroform. The product contained approximately 85% of polylactic acid, and the pendant polylactic acid average chain length was approximately 3.5.

The polymer was moulded at 100° C. to give a slab 1 cm.×0.2 cm.×0.2 cm. which was immersed in water at 37° C. The product absorbed water and became flexible, and eroded to give soluble products over a period of 2 months.

EXAMPLE 10

Mouse epidermal growth factor (285 μl. of a 21 mg./ml. solution in distilled water) was added to a solution of an 80/20 poly(D,L-lactide)/PEG 6000 copolymer of intrinsic viscosity 0.36 in chloroform, (45 mg.) in 2.5 ml. of 90% aqueous acetic acid. The solution of peptide and polymer was frozen and then freeze dried at ~0.01 mm.Hg. for 24 hours to give a dried product. The freeze dried material was moulded at 60° C. to give implants weighing 13.5 mg. and 15.3 mg. containing 1.3 and 1.5 mg. of peptide respectively.

These were implanted subcutaneously into 2 cats, each fitted with a gastric fistula. Blood samples were taken, and gastric acid output in response to a histamine stimulus was measured. Peptide was detected in the blood by radioimmunoassay for a minimum of 3 days subsequent to implantation, and gastric acid output showed inhibition of 3-6 days subsequent to implantation.

EXAMPLE 11

Mouse epidermal growth factor (120 μl. of 10.5 mg. peptide in 320 l. of distilled water) was added to a solution of an 85/15 poly(D,L-lactide)/PEG 6000 copolumer of intrinsic viscosity 0.39 in chloroform, (36 mg.) in 1.8 ml. of 90% aqueous acetic acid. The resultant solution was frozen and freeze-dried overnight. The freeze dried material was moulded at 70° C. to give an implant weighing 16.9 mg. (dimensions approximately 1×1×5 mm.).

Peptide was released from this implant continuously over at least 15 days into 10% human serum in water containing 0.1% sodium azide.

EXAMPLE 12

To show the effect of composition and hydrophilicity of the block copolymer on release of polypeptide from implants the following comparison was carried out.

In separate experiments implants were prepared using
(a) a block copolymer of intrinsic viscosity 0.39 in chloroform containing 25% w/w polyethylene glycol having a molecular weight of 6000 and 75% w/w of poly(D,L-lactide).
(b) a block copolymer of intrinsic viscosity 0.79 in chloroform containing 5% w/w polyethylene glycol having a molecular weight of 6000 and 95% w/w of poly(D,L-lactide).

76.2 mg. of polymer and ICI 118,630 (23.8 mg. as the acetate salt, equivalent to 20 mg. pure peptide) were dissolved in anhydride-free glacial acetic acid (1.5 ml.). The solution was frozen and freeze dried for 18 hours, and the freeze dried product was moulded at ~70° C. to give implants weighing ~45-50 mg. (dimensions approximately 0.2 cm.×0.2 cm.×1 cm.).

The implants were immersed in 1 ml. of McIlvains pH 7.4 buffer at 37° C., and 1 ml. samples of the aqueous medium were removed at given time points and assayed by high pressure liquid chromatography for drug content. The aqueous medium removed was replaced each time by 1 ml. of fresh buffer.

These release experiments showed that implants prepared using the more hydrophilic is polymer, containing 25% polyethylene glycol, released compounds for ~18 days.

In contrast, the implant prepared using the less hydrophilic copolymer, containing 5% polyethylene glycol, released compound continuously for at least 250 days.

EXAMPLE 13

Poly(ethylene glycol methyl ether) having a molecular weight of 5000 was purified as in Example 5.

20 G. of the purified poly(ethylene glycol methyl ether) was dried at 160° C./0.01 mm.Hg. for 1 hour. 80 G. of dry, freshly prepared D,L-lactide were added and the mixture stirred under a nitrogen atmosphere at 160° C. When all the D,L-lactide had melted, 0.15 ml. of stannous octoate (stannous-2-ethylhexanoate) were added, and the mixture was maintained at 160° C. for 6 hours, during which time a highly viscous product was formed. The mixture was allowed to cool, the flask was broken and the contents were dissolved in 200 ml. of acetone. The actone solution of polymer was added with vigorous stirring to 2000 ml. of hexane to precipitate the polymer. The precipitated polymer was dried at 70° C. under reduced pressure for 24 hours to give a block copolymer having an AB structure where A is polylactide and B is poly(ethylene glycol methyl ether).

This copolymer is particularly useful for preparing water-in-oil dispersions, which can be used to prepare microcapsules, or in microencapsulation procedures.

For example, 5 g. of the copolymer was dissolved in 200 ml. of methylene chloride, and 1 ml. of an aqueous solution of ICI.118,630 containing 20 mg. of compound was added with vigorous stirring, to produce a stable water in oil dispersion.

The water-in-oil emulsion was stirred vigorously and a non-solvent, such as hexane (2000 ml.) was added slowly to produce microcapsules, which were isolated by filtration, and dried, to give a drug/polymer mixture which even in this microcapsule or microencapsulated form gives sustained release over a period of several days.

The poly(ethylene glycol methyl ether) used in the above process was replaced by other derivatives of pol (ethylene glycol) to prepare similar block copolymers, and suitable examples are the monocetyl ethers (ceto macrogols) and stearate esters.

What we claim is:
1. A pharmaceutically or veterinarily acceptable amphipathic, non-cross-linked linear, branched or graft block copolymer, which has a minimum weight average molecular weight of 5,000, in which the hydrophobic component is biodegradable or hydrolytically unstable under normal physiological conditions, and the hydrophilic component may or may not be biodegradable, the coplymer being capable of absorbing water to form a hydrogel when placed in water or an aqueous physiological-type environment in an animal body, the amphipathic copolymer being a linear block copolymer of the formula $A_m(BA)_n$ or $B_m(AB)_n$ wherein m is 0 or 1, n is an integer, A is a pharmaceutically or veterinarily acceptable hydrophobic polymer and B is a pharmaceutically or veterinarily acceptable hydrophilic polymer, or the amphipathic copolymer is a graft or branched block copolymer of the formula $AB_n$ or $BA_n$ wherein A, B and n have the meanings stated above and wherein respectively either A or B is a backbone polymer with n units of a monomer or polymer B or A respectively grafted onto it, and wherein A is selected from poly (D-, L- and DL-lactic acids), poly (D-, L- and DL-lactides), polyglycolic acid, polyglycolide, poly- caprolactone, poly(3-hydroxy-butyric acid), non-therapeutic hydrophobic polypeptides, polyacetals of the formula:

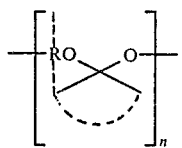

wherein R is a hydrocarbon radical, and n has the meaning stated above, polycarbonates or polyorthoesters of the formula:

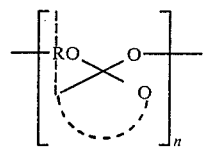

wherein R and n have the meanings stated above, and copolymers of the formula:

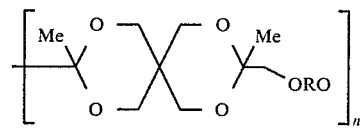

wherein R and n have the meanings stated above, and copolymers derived from two or more monomers from which the above polymers are derived; and the pharmaceutically or veterinarily acceptable hydrophilic polymer B is selected from polyvinyl alcohol, polyvinylpyrrolidone, polyethylene glycol, polyacrylamide, polymethacrylamide, dextran, alginic acid, sodium alginate, and gelatine, and copolymers of two or more of the monomers from which the above polymers are derived, and polyoxyethylene/polyoxypropylene block copolymers.

2. A copolymer as claimed in claim 1 wherein A is a polymer of a lactide.

3. A copolymer as claimed in claim 2 wherein A is a polymer of D,L-lactide and glycolide and B is polyethylene glycol.

4. A copolymer as claimed in claim 3 wherein the copolymer has the composition oxyethylene:lactic:glycol of 2:1:1.

* * * * *